United States Patent

Haga et al.

[11] Patent Number: 4,863,924
[45] Date of Patent: Sep. 5, 1989

[54] N-BENZOYL UREA COMPOUNDS, ANTITUMOROUS COMPOSITIONS CONTAINING THEM

[75] Inventors: Takahiro Haga; Nobutoshi Yamada; Hideo Sugi; Toru Koyanagi; Hiroshi Okada, all of Kusatsu, Japan

[73] Assignee: Ishihara Sangyo Kaisha Ltd., Osaka, Japan

[21] Appl. No.: 939,025

[22] Filed: Dec. 8, 1986

[30] Foreign Application Priority Data

Dec. 11, 1985 [JP]  Japan ................... 60-278180
Dec. 12, 1985 [JP]  Japan ................... 60-279884
Dec. 13, 1985 [JP]  Japan ................... 60-280694

[51] Int. Cl.$^4$ .................. A61K 31/505; A61K 31/50; C07D 237/14; C07D 239/34
[52] U.S. Cl. .................. 514/247; 514/274; 514/349; 514/351; 544/239; 544/241; 544/316; 544/317; 546/297; 546/300
[58] Field of Search .......... 544/239, 241, 297, 316, 544/317, 318; 514/247, 274, 349; 546/300

[56] References Cited

U.S. PATENT DOCUMENTS 4,677,110  6/1987  Haga et al. .................. 514/274

FOREIGN PATENT DOCUMENTS 0115210   8/1984  European Pat. Off. .
0164694  12/1985  European Pat. Off. .
0169484   1/1986  European Pat. Off. .
0178572   4/1986  European Pat. Off. .
0192235   8/1986  European Pat. Off. .
56-15272  2/1981  Japan .

OTHER PUBLICATIONS

Chemical Abstracts, vol. 98, 1983, p. 67, abstract No. 101183r Columbus, Ohio, U.S.; S. Garattini et al.: "Advance in Pharmacology and Chemotherapy" vol. 19, Academic Press, New York 1982, 294 pp.
Chemical Abstract, vol. 98 entry 101190r (1983) Ishihara.

Primary Examiner—John M. Ford
Attorney, Agent, or Firm—Oblon, Spivak, McClelland, Maier & Neustadt

[57] ABSTRACT

An N-benzoyl urea compound having the formula:

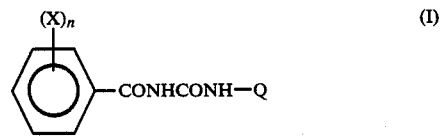

wherein X is a hydrogen atom, a halogen atom or a nitro group, n is an integer of from 1 to 3, and Q is

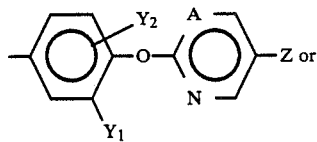

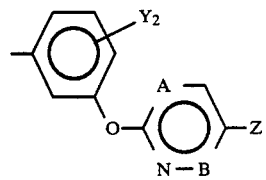

wherein $Y_1$ is an unsubstituted or substituted alkyl group, or an alkoxy or alkoxycarbonyl group with its alkyl moiety unsubstituted or substituted, $Y_2$ is a hydrogen atom, a halogen atom, a nitro group, an unsubstituted or substituted alkyl group, or an alkoxy or alkoxycarbonyl group with its alkyl moiety unsubstituted or substituted, Z is a hydrogen atom, a halogen atom, a trifluoromethyl group or a nitro group, and each of A and B is =CH— or a nitrogen atom, provided that one of A and B is =CH— and the other is a nitrogen atom, with the provisos (1) that when Q is

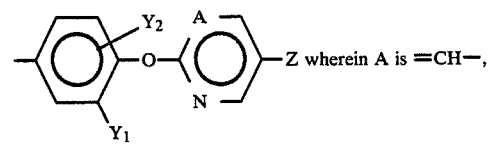

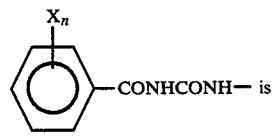

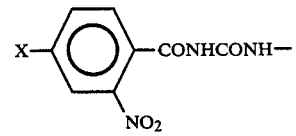

where when X is a hydrogen atom and $Y_1$ is an alkyl group, Z is not a hydrogen atom, a halogen atom nor a trifluoromethyl group, and (2) that when Q is

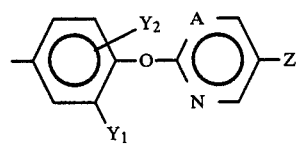

wherein A is a nitrogen atom and $Y_1$ is a trifluoromethyl group, $Y_2$ is other than a hydrogen atom.

11 Claims, No Drawings

N-BENZOYL UREA COMPOUNDS, ANTITUMOROUS COMPOSITIONS CONTAINING THEM

The present invention relates to novel N-benzoyl urea compounds, antitumorous compositions containing them as active ingredients, a method for treating a cancer by administering these compounds, and a process for preparing these compounds. More particularly, the present invention relates to the novel compounds including N-benzoyl-N'-[4-(2-pyrimidinyloxy or pyridyloxy)-phenyl]urea compounds, N-benzoyl-N'-[3-(2-pyrimidinyloxy)-phenyl]urea compounds and N-benzoyl-N'-[3-(3-pyridazinyloxy)-phenyl]urea compounds.

Compounds similar to the compounds of the present invention are disclosed in the following publications. Namely, N-benzoyl-N'-[4-(2-pyrimidinyloxy or pyridyloxy)phenyl]urea compounds are disclosed in Japanese Unexamined Patent Publication No. 109721/1982. However, they are different from the compounds of the present invention in the chemical structures with respect to the substituents on the phenyl rings directly linked to the urea group. Further, the compounds of the present invention are superior in the antitumorous activities to the compounds disclosed in the publication. With respect to N-benzoyl-N'-[3-(2-pyrimidinyloxy)-phenyl]urea compounds and N-benzoyl-N'-[3-(3-pyridazinyloxy)-phenyl]urea compounds, the applicants are aware of no prior art which discloses similar compounds. The closest prior art references may be Japanese Unexamined Patent Publications No. 35174/1983 and No. 72566/1983, U.S. Pat. No. 4,418,066 and U.K. Pat. No. 2.062,634. However, disclosed in these references are N-benzoyl-N'-[3-(phenoxy)-phenyl]urea compounds and N-benzoyl-N'-[3-(2-pyridyloxy)-phenyl]urea compounds, which are substantially different in their chemical structures from the compounds of the present invention, and which are disclosed to be useful merely as pesticides, particularly as insecticides, and there has been no disclosure or suggestion for antitumour activities.

The present inventors have conducted extensive research on N-benzoyl-N'-substituted phenyl urea compounds, particularly on the change of the substituents, and as a result, have found that novel N-benzoyl urea compounds having certain specific substituents have high antitumorous activities.

Further, the compounds of this type are generally hardly soluble in both water and organic solvents, and accordingly are poorly absorbed by the gut. Therefore, depending upon the manner of administration, they sometimes hardly exhibit antitumour activities, and there is a limitation for the intraperitoneal administration of such drugs for curing purposes. Whereas, it has been found that the compounds of the present invention are practically useful for the treatment of tumour or cancer and exhibit excellent antitumorous activities by a simple manner of administration and in a simple formulation for the administration without bringing about side effects. The present invention is based on these discoveries.

Namely, the present invention provides an N-benzoyl urea compound having the formula:

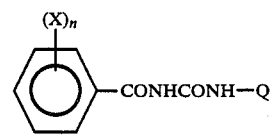

wherein X is a hydrogen atom, a halogen atom or a nitro group, n is an integer of from 1 to 3, and Q is

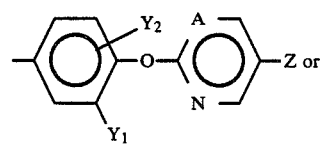

1wherein $Y_1$ is an unsubstituted or substituted alkyl group, or an alkoxy or alkoxycarbonyl group with its alkyl moiety unsubstituted or substituted, $Y_2$ is a hydrogen atom, a halogen atom, a nitro group, an unsubstituted or substituted alkyl group, or an alkoxy or alkoxycarbonyl group with its alkyl moiety unsubstituted or substituted, Z is a hydrogen atom, a halogen atom, a trifluoromethyl group or a nitro group, and each of A and B is=CH— or a nitrogen atom, provided that one of A and B is=CH— and the other is a nitrogen atom, with the provisos (1) that when Q is

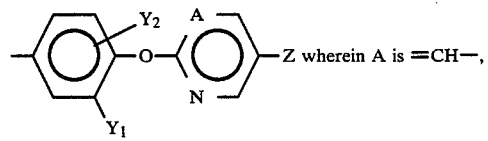

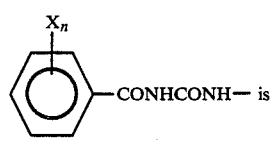

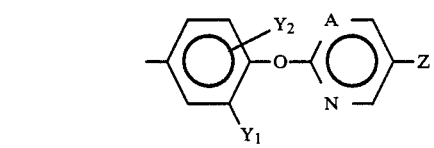

where when X is a hydrogen atom and $Y_1$ is an alkyl group, Z is not a hydrogen atom, a halogen atom nor a trifluoromethyl group, and (2) that when Q is wherein A is a nitrogen atom and $Y_1$ is a trifluoromethyl group, $Y_2$ is other than a hydrogen atom.

The present invention also provides an antitumorous composition containing such a compound as the active ingredient, a method for therapy of cancer by using such a compound, and a process for producing such a compound.

Now, the present invention will be described in detail with reference to the preferred embodiments.

In the above-mentioned formula I, when $Y_1$ or $Y_2$ is a substituted alkyl group, or an alkoxy or alkoxycarbonyl group with its alkyl moiety substituted, the alkyl group or the alkyl moiety may be substituted by one or more same or different substituents selected from the group consisting of halogen, alkoxy, alkylthio, cyano and thiocyanate. The alkyl group and the alkyl moiety may be of from 1 to 6 carbon atoms. Specifically, they may be methyl, ethyl, propyl, butyl, pentyl or hexyl.

The halogen atom in the formula I includes a fluorine atom, a chlorine atom, a bromine atom and an iodine atom.

Preferred among the compounds represented by the formula I are as follows.

(1) $(X)_n$ is one or two halogen atoms or nitro groups.

(2) $Y_1$ is an alkyl or alkoxy group which may be substituted by halogen, alkoxy, alkylthio, cyano or thiocyanate, more preferably an alkyl group which may be substituted by halogen, alkoxy or alkylthio, especially an alkyl group which may be substituted by halogen.

(3) $Y_2$ is a hydrogen atom or an alkyl or alkoxy group which may be substituted by halogen, alkoxy, alkylthio, cyano or thiocyanate, more preferably a hydrogen atom or an alkyl group.

(4) Q is

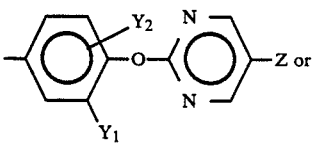

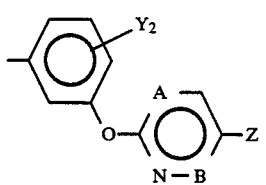

more preferably

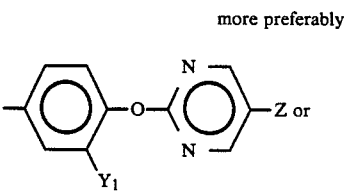

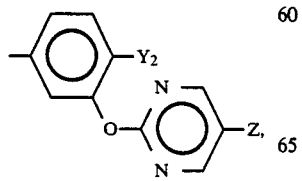

wherein Z is preferably a halogen atom.

The N-benzoyl urea compound of the formula I, may be prepared, for instance, by a process which comprises reacting a compound having the formula:

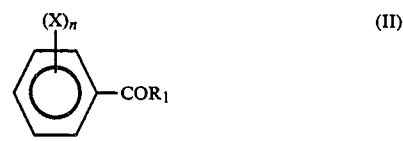

wherein $R_1$ is an isocyanate group, an amino group,

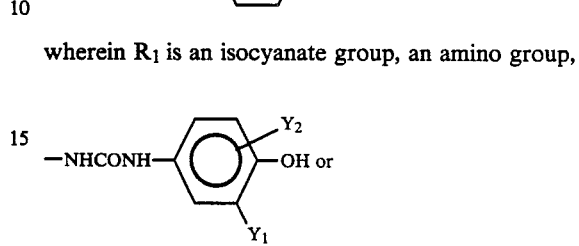

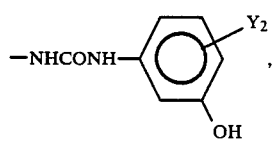

wherein X, $Y_1$, $Y_2$ and n are as defined above, with a compound having the formula:

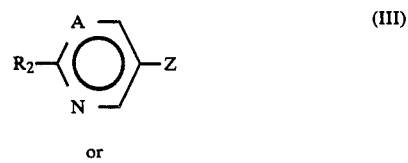

or

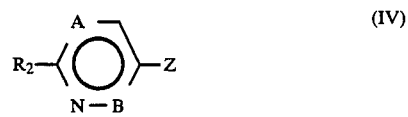

wherein $R_2$ is

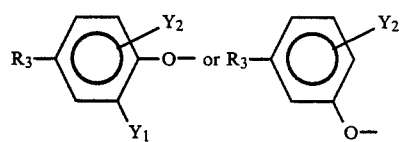

(wherein $Y_1$ and $Y_2$ are as defined above, and $R_3$ is an amino group or an isocyanate group which is different from $R_1$) or a halogen atom, provided that when $R_1$ is

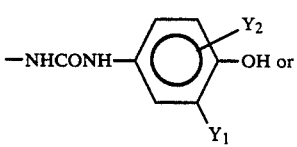

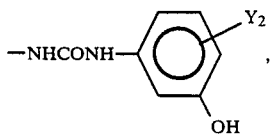

$R_2$ is a halogen atom, and when $R_1$ is an isocyanate group or an amino group, $R_2$ is

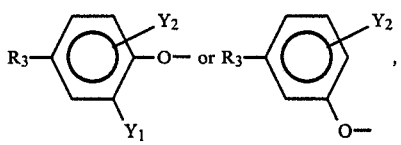

A, B and Z are as defined above.

The above process will now be described in detail.

[A-1]
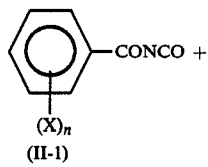

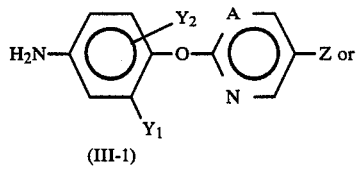

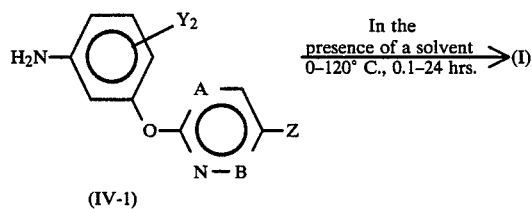

As the solvent to be used in the above reaction, there may be mentioned octane, benzene, toluene, xylene, monochlorobenzene, pyridine, dioxane, tetrahydrofuran, dimethyl sulfoxide, dimethylacetamide, ethyl acetate, acetone or methyl ethyl ketone.

[A-2]
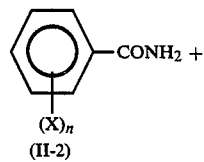

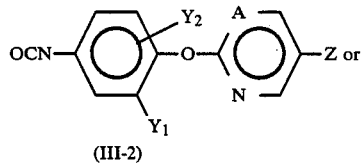

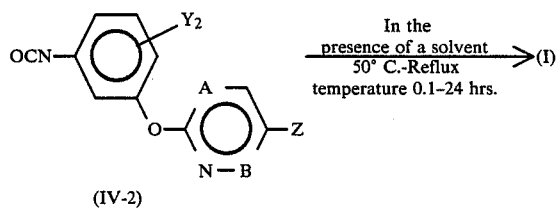

The solvent to be used in the above reaction, may be the same as used in the above reaction [A-1].

[A-3]
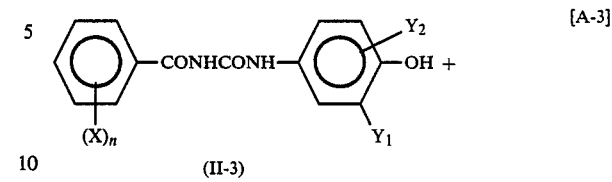

wherein Hal is a halogen atom.

As the alkaline substance to be used, there may be mentioned sodium hydroxide, potassium hydroxide, sodium carbonate, potassium carbonate, silver carbonate, sodium hydride, n-butyl lithium, etc. As the solvent, there may be mentioned an aprotic polar solvent such as dimethyl sulfoxide, dimethylformamide, hexamethylphosphoramide or sulfolane, a ketone such as acetone, methyl ethyl ketone or methyl isobutyl ketone, or a halogenated hydrocarbon such as methylene chloride or chloroform, etc.

[A-4]
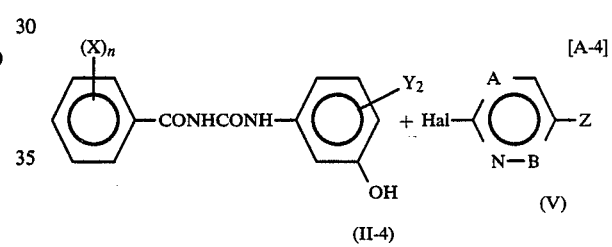

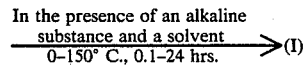

wherein Hal is a halogen atom.

The alkaline substance and the solvent may be the same as used in the above reaction [A-3]. The aniline compound of the formula III-1 used in the above reaction [A-1]may be prepared, for instance, by the following process.

[B-1]
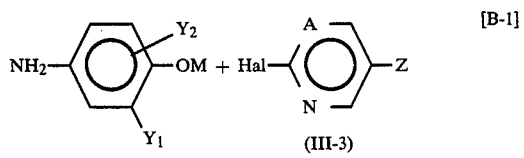

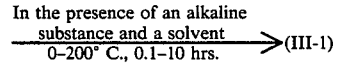

wherein Hal is a halogen atom, M is a hydrogen atom, potassium or sodium.

In the above reaction, when M is a hydrogen atom, the presence of the alkaline substance is required. The alkaline substance and the solvent used for the above reaction, may be the same as used for the above reaction It is preferred to conduct the condensation reaction in the presence of a nitrogen atmosphere.

[B-2]

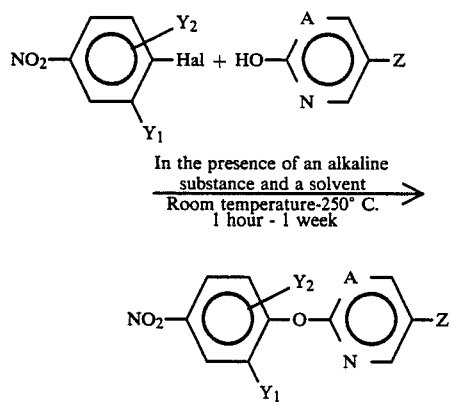

In the presence of an alkaline substance and a solvent
Room temperature-250° C.
1 hour - 1 week Reduced iron, glacial acetic acid
80° C.-Reflux temperature
0.1-1 hours ⟶ (III-1)

wherein Hal is a halogen atom.

The alkaline substance and the solvent used in the above reaction, may be the same as used in the above reaction.

[B-3]

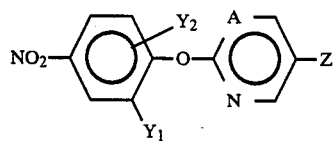 + (III-3)

Same as in Step [B-1] ⟶

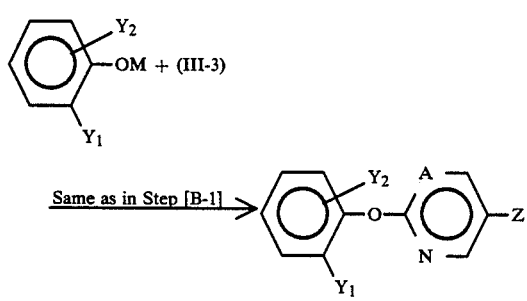

Concentrated sulfuric acid and nitric acid
−50° C.-100° C., 0.1-1 hour

Same as Step 2 of [B-2] ⟶ (III-1)

[B-4]

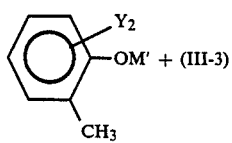 + (III-3)

Same as Step [B-1] ⟶

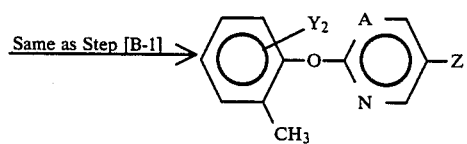

-continued

N—Chlorosuccinimide
BPO, CCl₄
60° C.-Reflux temperature
2-12 hrs.

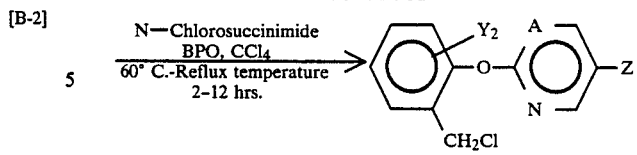

M'Y₁', Ethanol
20° C.-Reflux temperature
1-12 hrs.

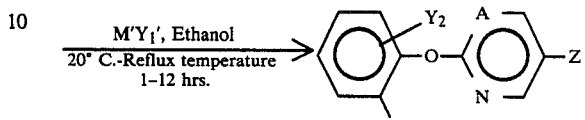

Same as Step 2 of [B-3] ⟶

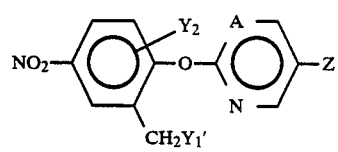

Same as Step 2 of [B-2] ⟶

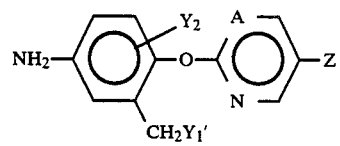

wherein M', is sodium or potassium, and Y₁', is a halogen atom, an alkoxy group, an alkylthio group, a cyano group or a thiocyanate group.

[B-5]

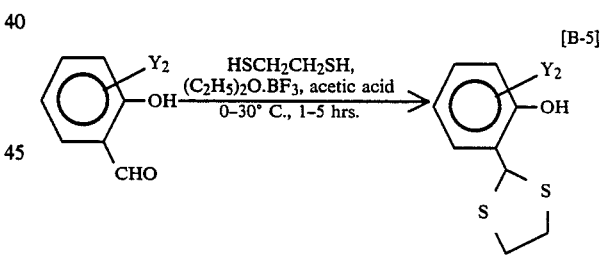

HSCH₂CH₂SH,
(C₂H₅)₂O.BF₃, acetic acid
0-30° C., 1-5 hrs.

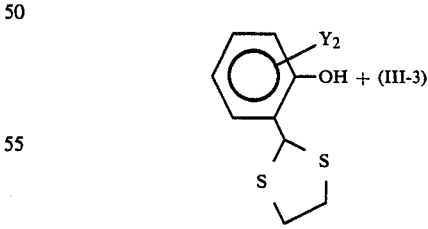 + (III-3)

Same as Step [B-1] ⟶

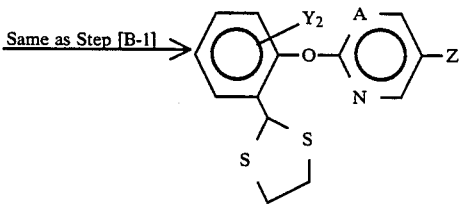

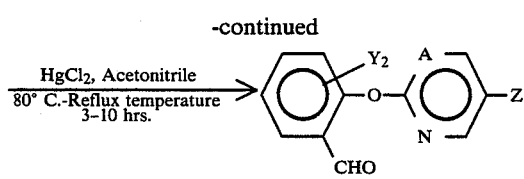

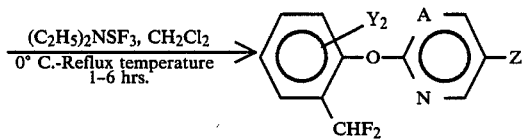

Same as Step 2 of [B-3]

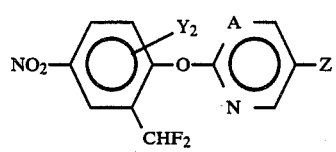

Same as Step 2 of [B-2]

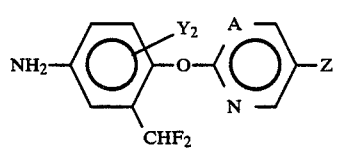

The isocyanate compound of the formula III-2 used for the above reaction, may be prepared, for instance, by the following method:

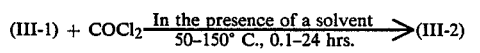   [B-6]

The solvent used must be inert to phosgene and may be the same as used in the above reaction, with the proviso that dimethylsulfoxide does not contain.

The N-benzoyl-N,-phenylurea compound of the formual II-3 used in the above reaction, may be prepared, for instance, by the following method:

[B-7]

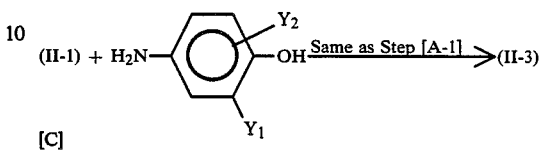

[C]

The aniline compound of the formula IV-1 used for the above reaction [A-1]may be prepared in the same manner as in the above reactions [B-1]to [B-5]from the corresponding starting materials. The isocyanate compound of the formula IV-2 and the urea compound of the formula II-4 used in the above reactions [A-2]and [A-4], respectively, may be prepared in the same manner as in the above reactions [B-6]and [B-7]. Among the intermediates for the preparation of the N-benzoyl urea compounds of the formula I, as described above, most of the compounds represented by the following formulas VI and VII are novel.

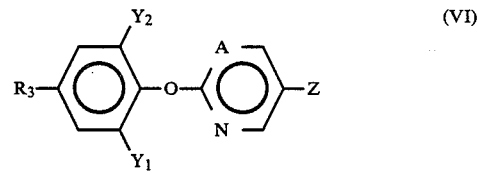   (VI)

wherein $R_3$, $Y_1$, $Y_2$ and Z are as defined above. Representative compounds of the formula VI will be listed in Table 1.

TABLE 1

| Intermediate No. | Formula VI | | | | | Physical properties Melting point (°C.) |
|---|---|---|---|---|---|---|
|  | $R_3$ | $Y_1$ | $Y_2$ | A | Z |  |
| 1 | $NH_2$ | $CH_3$ | H | N | Cl | 58–64 |
| 2 | " | " | " | " | Br | 103–108 |
| 3 | " | $COOCH_3$ | " | " | " | 139–140 |
| 4 | " | $C_2H_5$ | " | " | " | 82–87 |
| 5 | " | $CH_2OCH_3$ | " | " | " | 89–95 |
| 6 | " | $CH_2SCH_3$ | " | " | " | — |
| 7 | " | $CH_2CN$ | " | " | " | — |
| 8 | " | $CH_2SCN$ | " | " | " | — |
| 9 | " | $CHF_2$ | " | " | Cl | — |
| 10 | " | $OCH_3$ | " | " | " | 91–96 |
| 11 | " | $C_2H_5$ | " | " | " | 60–64 |
| 12 | " | $OCHF_2$ | " | " | " | — |
| 13 | " | $OCF_2CHFCF_3$ | " | " | " | — |
| 14 | " | $CH_3$ | " | " | H | — |
| 15 | " | " | " | " | $CF_3$ | — |
| 16 | " | " | " | " | $NO_2$ | — |
| 17 | $NH_2$ | $CH_2OCH_3$ | Cl | N | Br | — |
| 18 | " | $CH_3$ | $CH_3$ | " | " | 182–185 |
| 19 | " | " | $C_2H_5$ | " | " | — |
| 20 | NCO | " | H | " | " | — |
| 21 | $NH_2$ | $CF_3$ | Cl | " | " | Viscous oil |
| 22 | " | $CH_3$ | $CH_2OCH_3$ | " | " | " |
| 23 | " | " | $COOCH_3$ | " | " | — |
| 24 | " | $CF_3$ | H | =CH— | Cl | — |
| 25 | " | $CH_3$ | " | " | $NO_2$ | 76–79 |
| 26 | " | " | " | " | Br | 70–74 |
| 27 | " | $CF_3$ | " | " | " | — |
| 28 | " | " | " | " | $CF_3$ | — |
| 29 | " | " | " | " | H | — |

TABLE 1-continued

| Intermediate No. | Formula VI | | | | Physical properties Melting point (°C.) |
|---|---|---|---|---|---|
| | $R_3$ | $Y_1$ | $Y_2$ | A | Z | |
| 30 | " | $CF_2H$ | " | " | Cl | — |

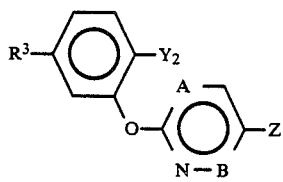

(VII)

wherein $R_3$, $Y_2$, A, B and Z are as defined above.

Representative compounds of the formula VII will be shown in Table 2.

TABLE 2

| Intermediate No. | Formula VII | | | | | Physical properties Melting point (°C.) |
|---|---|---|---|---|---|---|
| | $R_3$ | $Y_2$ | A | B | Z | |
| 31 | $NH_2$ | $CH_3$ | N | CH | Cl | 86–91 |
| 32 | " | H | " | " | Br | $n_D^{21.4}1.6462$ |
| 33 | " | $C_2H_5$ | " | " | " | $n_D^{30.2}1.6164$ |
| 34 | " | " | " | " | Cl | $n_D^{22.4}1.5998$ |
| 35 | " | $CH_3$ | CH | N | " | 116–118 |
| 36 | " | F | N | CH | I | — |
| 37 | " | Cl | " | " | Br | — |
| 38 | " | $NO_2$ | " | " | " | — |
| 39 | " | $OCH_3$ | " | " | " | — |
| 40 | " | $CF_3$ | " | " | " | — |
| 41 | " | $CH_2OCH_3$ | " | " | $NO_2$ | — |
| 42 | $NH_2$ | $CH_2OCH_3$ | N | CH | $CF_3$ | — |
| 43 | " | $CH_3$ | " | " | H | — |
| 44 | " | " | " | " | Br | Oily substance |
| 45 | NCO | " | " | " | Cl | — |
| 46 | $NH_2$ | $CH_2CN$ | " | " | Br | — |
| 47 | " | $COOCH_3$ | " | " | " | — |

Note:
The physical properties of intermediates Nos. 32–34 are refractive indices.

The following compounds may be mentioned as compounds similar to those of Table 2.

Intermediate No. 48: 2-methyl-3-(5-chloro-2-pyrimidinyloxy)anile

Intermediate No. 49: 2-methyl-3-(5-bromo-2-pyrimidinyloxy)anile

Now, the present invention will be described in further detail with reference to Examples. However, it should be understood that the present invention is by no means restricted by these specific Examples.

SYNTHETIC EXAMPLE 1

Synthesis of Compound No. 1

N-(2-nitrobenzoyl)-N'-[3-(5-chloro-2-pyrimidinyloxy)-4-methylphenyl]urea (1) A mixture of 19.8 g of 5-amino-2-methylphenol, 37 g of potassium carbonate, 20 g of 2,5-dichloropyrimidine and 200 ml of dimethylsulfoxide, was reacted in a nitrogen atmosphere at 100° C. for 1.5 hours.

After the completion of the reaction, the product was poured into water, and extracted with ethyl acetate. The extract was washed with a saturated sodium chloride aqueous solution, dried over anhydrous sodium sulfate, and then purified by silica gel column chromatography, to obtain 30 g of 3-(5-chloro-2-pyrimidinyloxy)-4methylaniline having a melting point of from 86° to 91° C.

(2) A solution obtained by dissolving 20 g of 3-(5-chloro-2-pyrimidinyloxy)-4-methylaniline obtained in the above step (1) in 100 ml of dioxane was added to 19.6 g of 2-nitrobenzoylisocyanate, and the mixture was reacted at room temperature for 18 hours.

After the completion of the reaction, the product was poured into water, and washed with hot water at 50° C. and then with methyl alcohol, to obtain 33.6 g of the desired product having a melting point of from 214° to 219° C.

SYNTHETIC EXAMPLE 2

Synthesis of Compound No. 8:

N-(2-nitrobenzoyl)-N'-[3-(6-chloro-3-pyridazinyloxy)-4-methylphenyl]urea (1) A mixture of 4.0 g of 3,6-dichloropyridazine, 3.3 g of 5-amino-2-methylphenol, 3.73 g of potassium carbonate and 40 ml of dimethylsulfoxide, was reacted in a nitrogen atmosphere at 120° C. for 1 hour.

After the completion of the reaction, the product was poured into water, and extracted with ethyl acetate. The extract was washed with a saturated sodium chloride aqueous solution, dried over anhydrous sodium sulfate and after distilling off the solvent, purified by silica gel column chromatography, to obtain 3.4 g of 3-(6-chloro-3-pyridazinyloxy)-4-methylaniline having a melting point of from 116° to 118° C.

(2) A solution obtained by dissolving 2.0 g of 3-(6-chloro-3-pyridazinyloxy)-4-methylaniline obtained in the above step (1) in 20 ml of dioxane was added to 1.95 g of 2-nitrobenzoylisocyanate, and the mixture was reacted at room temperature for 17 hours.

After the completion of the reaction, the product was poured into water, and extracted with ethyl acetate. The extract was dried over anhydrous sodium sulfate, and the solvent was distilled off. The residue was purified by silica gel column chromatography to obtain 3.43 g of the desired product having a melting point of from 231° to 236° C.

SYNTHETIC EXAMPLE 3

Synthesis of Compound No. 9:

N-(2-nitrobenzoyl)-N'-[4-fluoro-3-(5-iodo-2-pyrimidinyloxy)phenyl]urea (1) A mixture of 2.0 g of 2-chloro-5-iodoprimidine, 1.03 g of 2-fluorophenol, 2.30g of potassium carbonate and 20 ml of dimethylsulfoxide, was reacted at 100° C. for 1 hour.

After the completion of the reaction, the product was poured into water, and extracted with ethyl acetate. The extract was dried over anhydrous sodium sulfate, and the solvent was distilled off to obtain 2.56 g of 2-(2-fluorophenoxy)-5-iodopyrimidine.

(2) 2.56 g of 2-(2-fluorophenoxy)-5-iodopyrimidine obtained in the above step (1), was dissolved in 10 ml of concentrated sulfuric acid, and an acid mixture of 0.68 ml of 60% nitric acid and 2 ml of concentrated sulfuric acid, was slowly dropwise added at room temperature for reaction.

After the completion of the reaction, the reaction product was poured into ice water, and extracted with ethyl acetate. The extract was dried over anhydrous sodium sulfate, and the solvent was distilled off. The residue was purified by silica gel column chromatography, iodopyrimidine.

(3) 1.60 g of 2-(2-fluoro-5-nitrophenoxy)-5-iodopyrimidine obtained in the above step (2), was added to 10 ml of glacial acetic acid, and heated to 90° C., and then 1.24 g of reduced iron was gradually added thereto. The mixture was refluxed for 5 minutes, and then returned to room temperature. A solvent mixture of acetone and water, was added thereto, and the mixture was filtered. The solvent in the filtrate was distilled off, and the residue thus obtained was poured into water, and extracted with ethyl acetate. The extract was dried over anhydrous sodium sulfate, and the solvent was distilled off. The residue was purified by silica gel column chromatography to obtain 1.31 g of 3-(5-iodo-2-pyrimidinyloxy)-4-fluoroaniline. (4) A solution obtained by dissolving 1.31 g of 3-(5-iodo-2-pyrimidinyloxy)-4-fluoroaniline obtained in the above step (3) in 20 ml of dioxane, was added to 1.15 g of 2-nitrobenzoylisocyanate, and the mixture was reacted at room temperature for 15 hours.

After the completion of the reaction, the product was poured into warm water of 50° C., subjected to filtration, washed with warm water of 50° C., then suspended in ethyl acetate, and after an addition of n-hexane, subjected to filtration, to obtain 1.80 g of the desired product having a melting point of from 220° to 221° C.

SYNTHETIC EXAMPLE 4

Synthesis of Compound No. 23

N-(2-nitrobenzoyl)-N'-[4-(5-chloro-2-pyrimidinyloxy)-3-methylphenyl]urea (1) A mixture of 2.0 g of 4-amino-2-methylphenol, 3.7 g of potassium carbonate, 2.0 g of 2,5-dichloropyrimidine and 20 ml of dimethylsulfoxide, was reacted in a nitrogen atmosphere at 100° C. for 2 hours.

After the completion of the reaction, the product was poured into water and extracted with ethyl acetate. The extract was washed with a saturated sodium chloride aqueous solution, dried over anhydrous sodium sulfate, and purified by silica gel column chromatography, to obtain 2.0 g of 4-(5-chloro-2-pyrimidinyloxy)-3-methylaniline having a refractive index ($n_D^{22.4}$) of 1.6105.

(2) Into a flask, 2.12 g of 2-nitrobenzoylisocyanate was introduced, and a solution obtained by dissolving 2.00 g of 4-(5-chloro-2-pyrimidinyloxy)-3-methylaniline obtained in the above step (1) in 30 ml of dioxane, was added thereto. The mixture was reacted at room temperature for 14 hours.

After the completion of the reaction, the product was poured into warm water of 50° C., and subjected to filtration. Crystals thus obtained were washed with warm water of 50° C., then suspended in ethyl acetate, and after an addition of n-hexane, subjected to filtration, to obtain 2.82 g of the desired product having a melting point of from 204° to 206° C.

SYNTHETIC EXAMPLE 5

Synthesis of Compound No. 30

N-(2-nitrobenzoyl)-N'-[4-(5-bromo-2-pyrimidinyloxy)3-methoxymethylphenyl]urea (1) A mixture of 2.2 g of 2-chloro-6-methoxymethyl-4nitrophenol, 0.30 g of 10% palladium carbon, 11.5 g of magnesium oxide, 20 ml of ethyl alcohol and 30 ml of water, was reacted under a hydrogen pressure of 4 atm. for 10 hours under shaking.

After the completion of the reaction, acetone was added to the product, and the mixture was filtered to obtain a filtrate, which was subjected to distillation under reduced pressure. To the residue thus obtained, acetone was added, and the mixture was filtered to obtain a filtrate, which was again subjected to distillation under reduced pressure. The residue was purified by silica gel column chromatography to obtain 1.27 g of 4-amino-2-methoxymethylphenol having a melting point of from 121° to 126° C.

(2) A mixture of 1.60 g of 5-bromo-2-chloropyrimidine, 1.27 g of 4-amino-2-methoxymethylphenol, 2.30 g of potassium carbonate and 30 ml of dimethylsulfoxide, was reacted in a nitrogen atmosphere at 100° C. for 1 hour.

After the completion of the reaction, the product was poured into water, and extracted with ethyl acetate. The extract was washed with a saturated sodium chloride aqueous solution, then dried over anhydrous sodium sulfate, and purified by silica gel column chromatography to obtain 1.38 g of 4-(5-bromo-2-pyrimidinyloxy)-3methoxymethylaniline having a melting point of from 89 to 95° C. (3) A solution obtained by dissolving 1.38 g of 4-(5-bromo-2-pyrimidinyloxy)-3-methoxymethylaniline obtained in the above step (2) in 10 ml of dioxane, was dropwise added to a solution of 1.04 g of 2-nitrobenzoylisocyanate in 10 ml of dioxane, and the mixture was reacted at room temperature for 17 hours.

After the completion of the reaction, the product was poured into water, and extracted with ethyl acetate. The extract was dried over anhydrous sodium sulfate, and then ethyl acetate was distilled off. The residue was subjected to silica gel column chromatography, and crystals thus obtained was washed with methanol, then dissolved in dimethyl sulfoxide, and poured into water, followed by filtration to obtain 1.66 g of the desired product having a melting point of from 187° to 189° C.

SYNTHETIC EXAMPLE 6

Synthesis of Compound No. 34

N-(2-nitrobenzoyl)-N'-[4-(5-chloro-2-pyrimidinyloxy)-3-difluoromethylphenylurea]

(1) 15 g of salicylaldehyde and 13.9 g of 1,2-ethanedithol were dissolved in 100 ml of acetic acid, and 12 ml of boron trifluoride (an ether complex) was gradually dropwise added thereto under cooling with ice.

After the completion of the dropwise addition, the mixture was reacted at room temperature for 1 hour under stirring.

After the completion of the reaction, acetic acid was distilled off under reduced pressure. To the residue, ethyl acetate and water were added for extraction. The extract was washed with a saturated aqueous solution of sodium hydrogen carbonate and sodium chloride, and dried over anhydrous sodium sulfate. Then, the solvent was distilled off to obtain 22.8 g of 2-(2-hydroxyphenyl)-1,3-dithiolan.

(2) 8.5 g of 2,5-dichloropyrimidine, 12.4 g of 2-(2-hydroxyphenyl)-1,3-dithiolan obtained in the above step (1) and 10 g of potassium carbonate were dissolved in 50 ml of dimethylformamide, and reacted at 100° C. under stirring.

After the completion of the reaction, the product was poured into ice water, and extracted with ethyl acetate. The extract was washed with water and a saturated sodium chloride aqueous solution, and dried over anhydrous sodium sulfate. The solvent was distilled off, and the residue was purified by silica gel column chromatography to obtain 14.6 g of 2-[2-(5-chloro-2-pyrimidinyloxy)phenyl]-1,3-dithiolan.

(3) 28.7 g of mercuric chloride was dissolved in a solvent mixture of 300 ml of acetonitrile and 60 ml of water, and then a solution obtained by dissolving 14.9 g of the dithiolan obtained in the above step (2) in 160 ml of acetonitrile and 12 ml of water, was gradually dropwise added under stirring.

After the completion of the dropwise addition, the mixture was stirred at room temperature until the starting materials disappeared. Then, the temperature was raised to the refluxing temperature, and the reaction was conducted for 4 hours.

After the completion of the reaction, insoluble materials were filtered off from the reaction product, and the solvent was distilled off under reduced pressure. The residue thus obtained was extracted by an addition of methylene chloride and water. The extract was washed with a saturated sodium chloride aqueous solution, and dried over anhydrous sodium sulfate. Then, the solvent was distilled off under reduced pressure, and the residue was purified by silica gel column chromatography to obtain 5.5 g of 2-(5-chloro-2-pyrimidinyloxy)benzaldehyde.

(4) A methylene chloride solution (5 ml) of 2.5 g of the benzaldehyde obtained in the above step (3) was gradually dropwise added at room temperature to a solution obtained by dissolving 1.9 g of diethylamino sulfur trifluoride in 15 ml of methylene chloride. After the completion of the dropwise addition, the mixture was stirred at room temperature for 1 hour under stirring.

After the completion of the reaction, the reaction product was poured into ice water and extracted with methylene chloride. The extract was washed with a saturated sodium chloride aqueous solution, and dried over anhydrous sodium sulfate. Then, the solvent was distilled off, and the residue was purified by silica gel column chromatography to obtain 1.1 g of 2-(5-chloro-2-pyrimidinyloxy)-benzalfluoride.

(5) A mixture of 0.85 ml of concentrated nitric acid and 0.85 ml of concentrated sulfuric acid, was dropwise added and reacted to a solution obtained by dissolving 2.2 g of the benzalfluoride obtained in the above step (4) in 15 ml of concentrated sulfuric acid under cooling with ice, while maintaining the temperature at a level of from 0° to 5° C.

After the completion of the reaction, the product was poured into ice water, and extracted with methylene chloride. The extract was washed with a saturated aqueous solution of sodium hydrogen carbonate and sodium chloride, and dried over anhydrous sodium sulfate. Then, the solvent was distilled off, and the residue was purified by silica gel column chromatography to obtain 1.7 g of 2-(5-chloro-2-pyrimidinyloxy)-5-nitrobenzalfluoride.

(6) 1.7 g of the nitrobenzodifluoride obtained in the above step (5) was dissolved in 50 ml of acetic acid, and then the solution was heated to 90° C. Then, 2.3 g of reduced iron was gradually added and reacted thereto under stirring.

After the completion of the reaction, insoluble matters were filtered off from the reaction product, and the filtrate was extracted by an addition of methylene chloride and water. The extract was washed with a saturated solution of sodium hydrogen carbonate and sodium chloride, and then dried over anhydrous sodium sulfate. Then, the solvent was distilled off, and the residue was purified by silica gel column chromatography to obtain 0.96 g of 5-amino-2-(5-chloro-2-pyrimidinyloxy)-benzalfluoride.

(7) A dioxane solution (10 ml) of 0.96 g of the amino benzalfluoride obtained in the above step (6) was gradually dropwise added at room temperature to a dioxane solution (5 ml) of 0.74 g of 2-nitrobenzoylisocyanate prepared from 2-nitrobenzamide. After the completion of the dropwise addition, the mixture was reacted at room temperature for 1 hour under stirring.

After the completion of the reaction, dioxane was distilled off under reduced pressure, and the residue was recrystallized from methylene chloride to obtain 0.9 g of N-(2-nitrobenzoyl)-N'-[4-(5-chloro-2-pyrimidinyloxy)-3-difluoromethylphenyl]urea having a melting point of from 185° to 186° C.

SYNTHETIC EXAMPLE 7

Synthesis of Compound No. 24

N-(2-nitrobenzoyl)-N'-[4-(5-bromo-2-pyrimidinyloxy)-3-methylphenyl]urea (1) 4-(5-bromo-2-pyrimidinyloxy)-3-methylaniline was obtained in the same manner as in Synthetic Example 5(2) except that 1.27 g of 4-amino-2-methoxymethylphenol was changed to 1.02 g of 4-amino-2-methylphenol.

(2) A solution obtained by dissolving 1.7 g of the aniline obtained in the above step (1) in 5 ml of ethyl acetate, was dropwise added at room temperature to a solution of 0.01 mol of phosgene in 15 ml of ethyl acetate, and the mixture was reacted at room temperature for 3 hours under stirring and under reflux for further 1 hour.

After the completion of the reaction, ethyl acetate was distilled off under reduced pressure, and the residue was vacuum-dried to obtain 1.8 g of 4-(5-bromo-2-pyrimidinyloxy)-3-methylphenylisocyanate.

(3) To a solution obtained by dissolving 1.8 g of the isocyanate obtained in the above step (2) in 20 ml of toluene, 0.98 g of 2-nitrobenzamide was added under stirring, and the mixture was reacted under reflux for 4 hours.

After the completion of the reaction, 10 ml of methanol was added to the product, and the mixture was cooled. Precipitated crystals were collected by filtration to obtain 1.20 g of the desired product.

SYNTHETIC EXAMPLE 8

Synthesis of Compound No. 37

N-(2-nitrobenzoyl)-N'-[4-(5-chloro-2-pyrimidinyloxy)-3-ethylphenyl]urea (1) A solution obtained by dissolving 5.78 g of 2-nitrobenzoylisocyanate in 10 ml of dioxane, is dropwise added at room temperature to a solution obtained by dissolving 4.12 g of 4-amino-2-ethylphenol in 100 ml of dioxane, and the mixture is reacted at room temperature for 12 hours under stirring.

After the completion of the reaction, the product is poured into water, and precipitated crystals are collected by filtration and washed with methanol to obtain N-(3-ethyl-4-hydroxyphenyl)-N'-(2-nitrobenzoyl)urea.

(2) To a solution obtained by dissolving the urea obtained in the above step (1) in 100 ml of dimethylsulfoxide, 1.4 g of potassium hydroxide is added, and 4.9 g of 2,5-dichloropyrimidine is further added. The mixture is reacted at 50° C. for 5 hours.

After the completion of the reaction, 200 ml of methanol is added to the reaction product, and precipitated crystals are collected by filtration. The crystals are washed with water and methanol to obtain the desired product.

SYNTHETIC EXAMPLE 9

Synthesis of Compound No. 51

N-(2-nitrobenzoyl)-N'-[4-(5-chloro-2-pyridyloxy)-3-trifluoromethylphenyl]urea (1) A mixture of 10 g of 5-chloro-2-pyridone, 14.3 g of 2-chloro-5-nitrobenzotrifluoride, 26.6 g of potassium carbonate and 60 ml of dimethylsulfoxide, was reacted at 100° C. for 2 hours.

After the completion of the reaction, the product was poured into 70 ml of ethyl ether, washed twice each sequentially with water, a 10% sodium hydroxide aqueous solution and a saturated sodium chloride aqueous solution, and then dried over anhydrous sodium sulfate. Then, the solvent was distilled off, and the residue was purified by silica gel column chromatography to obtain 6.4 g of 2-(5-chloro-2-pyridyloxy)-5-nitrobenzotrifluoride.

(2) 6 g of 2-(5-chloro-2-pyridyloxy)-5-nitrobenzotrifluoride obtained in the above step (1) was dissolved in 40 ml of glacial acetic acid, and 6.3 g of reduced iron was added thereto under vigorous stirring. The mixture was reacted for 30 minutes.

After the completion of the reaction, insoluble matters were filtered off from the reaction product, and the solvent was distilled off. The residue thus obtained was dissolved in 80 ml of methylene chloride, washed twice with an aqueous sodium hydrogen carbonate solution, and dried over anhydrous sodium sulfate. The solvent was distilled off to obtain 4.2 g of 4-(5-chloro-2-pyridyloxy)-3-trifluoromethylaniline.

(3) A solution obtained by dissolving 1.6 g of 2-nitrobenzoylisocyanate in 5 ml of dioxane, was dropwise added to a solution obtained by dissolving 2.0 g of 4-(5-chloro-2-pyridyloxy)-3-trifluoromethylaniline obtained in the above step (2) in 8 ml of dioxane, and the mixture was reacted at room temperature overnight.

After the completion of the reaction, the reaction product was poured into water, filtered, and washed with methanol. Crystals thus obtained were dissolved in ethyl acetate, and insoluble matters were filtered off. Then, n-hexane was added thereto for crystallization to obtain 3.1 g of the desired product having a melting point of from 196° to 198° C.

SYNTHETIC EXAMPLE 10

Synthesis of Compound No. 55

N-(2,4-dinitrobenzoyl)-N'-[3-trifluoromethyl-4-(5-trifluoromethyl-2-pyridyloxy)phenyl]urea (1) A mixture of 6 g of 2-trifluoromethylphenol, 5.9 g of 2-chloro-5-trifluoromethylpyridine, 9.6 g of potassium carbonate and 40 ml of dimethylsulfoxide, was reacted at 100° C. for 4 hours.

After the completion of the reaction, the reaction product was poured into 70 ml of ethyl ether, washed twice each sequentially with water, a 10% sodium hydroxide aqueous solution, and a saturated sodium chloride aqueous solution, and dried over anhydrous sodium sulfate. The solvent was distilled off to obtain 8.2 g of 2-(5-trifluoromethyl-2-pyridyloxy)benzotrifluoride.

(2) 8 g of 2-(5-trifluoromethyl-2-pyridyloxy)benzotrifluoride obtained in the above step (1), was dissolved in 45 ml of concentrated sulfuric acid, and after cooling the solution to 0° C., 3.3 g of 60% nitric acid was dropwise added thereto at a temperature of from 0° to 5° C. After the completion of the dropwise addition, the mixture was reacted at a temperature of from 0° to 5° C. for 1 hour under stirring.

After the completion of the reaction, the reaction product was poured into water, and extracted twice with methylene chloride. The extract was washed twice with a saturated sodium chloride aqueous solution, and dried over anhydrous sodium sulfate. The solvent was distilled off to obtain 7.2 g of 2-(5-trifluoromethyl-2-pyridyloxy)-5-nitrobenzotrifluoride.

(3) 7 g of 2-(5-trifluoromethyl-2-pyridyloxy)-5-nitrobenzotrifluoride obtained in the above step (2) was dissolved in 50 ml of glacial acetic acid, and 6.7 g of reduced iron was added under vigorous stirring. The mixture was reacted for 30 minutes.

After the completion of the reaction, insoluble matters were filtered off from the reaction product, and the solvent was distilled off. The residue thus obtained was dissolved in 80 ml of methylene chloride, then washed twice with an aqueous sodium hydrogen carbonate solution, and dried over anhydrous sodium sulfate. Then, the solvent was distilled off, and the residue was purified by silica gel column chromatography to obtain 2.7 g of 4-(5-trifluoromethyl-2-pyridyloxy)-3-trifluoromethylaniline.

(4) A solution obtained by dissolving 1.4 g of 2,4-dinitrobenzoylisocyanate in 5 ml of dioxane, was dropwise added to a solution obtained by dissolving 1.5 g of 4-(5-trifluoromethyl-2-pyridyloxy)-3trifluoromethylaniline obtained in the above step (3) in 8 ml of dioxane, and the mixture was reacted at room temperature overnight.

After the completion of the reaction, the reaction product was poured into water, and filtered. Crystals thus obtained were dissolved in ethyl acetate, and insoluble matters were filtered off. Then, n-hexane was added thereto for crystallization, to obtain 1.8 g of the desired product having a melting point of from 235 to 238° C.

Now, representative compounds of the present invention, are shown in Tables 3 and 4.

TABLE 3

$(X)_n$-C6H4-CONHCONH-Q_1 (Q_1: 2,6-disubstituted phenyl-O-pyridine with A, B, Z substituents)

| Compound No. | $(X)_n$ | $Y_2$ | A | B | Z | Melting point (°C.) |
|---|---|---|---|---|---|---|
| 1 | 2-NO_2 | CH_3 | N | CH | Cl | 214–219 |
| 2 | " | H | " | " | Br | 207–210 |
| 3 | " | C_2H_5 | " | " | " | 223–227 |
| 4 | 2-Cl | " | " | " | Cl | 174–179 |
| 5 | 2-NO_2 | " | " | " | " | 224–228 |
| 6 | 4-Cl,2-NO_2 | " | " | " | " | 199–205 |
| 7 | 2,4-(NO_2)_2 | " | " | " | " | 224–228 |
| 8 | 2-NO_2 | CH_3 | CH | N | " | 231–236 |
| 9 | " | F | N | CH | I | 220–221 |
| 10 | " | Cl | " | " | Br | — |
| 11 | 2-NO_2 | NO_2 | " | " | " | — |
| 12 | " | OCH_3 | " | " | " | — |
| 13 | " | CF_3 | " | " | " | — |
| 14 | 2-NO_2 | CH_2OCH_3 | N | CH | NO_2 | — |
| 15 | " | CH_2SCH_3 | " | " | CF_3 | — |
| 16 | 4-Cl,2-NO_2 | CH_3 | " | " | Cl | 188–190 |
| 17 | 2,4-(NO_2)_2 | " | " | " | " | 199–202 |
| 18 | 4,6-Cl_2,2-NO_2 | " | " | " | " | — |
| 19 | 2-NO_2 | " | " | " | H | — |
| 20 | " | " | " | " | Br | 230–232.5 |
| 21 | " | CH_2CN | " | " | " | — |
| 22 | " | COOCH_3 | " | " | " | — |

TABLE 4

$(X)_n$-C6H4-CONHCONH-Q_2 (Q_2: 2,6-disubstituted phenyl with $Y_1$, $Y_2$ -O- pyridine A, Z)

| Compound No. | $(X)_n$ | $Y_1$ | $Y_2$ | A | Z | Melting point (°C.) |
|---|---|---|---|---|---|---|
| 23 | 2-NO_2 | CH_3 | H | N | Cl | 204–206 |
| 24 | " | " | " | " | Br | 214–217 |
| 25 | " | COOCH_3 | " | " | " | 200–201 |
| 26 | 2-Cl | CH_3 | " | " | " | 204–205 |
| 27 | 4-Cl,2-NO_2 | " | " | " | " | 229–235 |
| 28 | 2,4-(NO_2)_2 | " | " | " | " | 232–235 |
| 29 | 2-NO_2 | C_2H_5 | " | " | " | 211–212.5 |
| 30 | " | CH_2OCH_3 | " | " | " | 187–189 |
| 31 | " | CH_2SCH_3 | " | " | " | 200–201 |
| 32 | " | CH_2CN | " | " | " | 231–233 |
| 33 | " | CH_2SCN | " | " | " | 189–190 |
| 34 | " | CHF_2 | " | " | Cl | 185–186 |
| 35 | " | OCH_3 | " | " | " | 219–221 |
| 36 | 2-Cl | CH_3 | " | " | " | 197–199 |
| 37 | 2-NO_2 | C_2H_5 | H | N | Cl | 181–184 |
| 38 | " | OCHF_2 | " | " | " | 217–219 |
| 39 | " | OCF_2CHFCF_3 | " | " | " | 75–79 |
| 40 | H | CH_3 | " | " | " | — |
| 41 | 2-NO_2 | " | " | " | H | — |
| 42 | " | " | " | " | CF_3 | — |
| 43 | " | " | " | " | NO_2 | — |
| 44 | 4,6-Cl_2,2-NO_2 | " | " | " | Cl | — |
| 45 | 2-NO_2 | CH_2OCH_3 | Cl | " | Br | 236–238 |
| 46 | " | CH_3 | CH_3 | " | " | 248–249.5 |
| 47 | " | " | C_2H_5 | " | " | — |
| 48 | " | CF_3 | Cl | " | " | 221–224 |
| 49 | " | CH_3 | CH_2OCH_3 | " | " | 208–210 |
| 50 | " | " | COOCH_3 | " | " | — |
| 51 | 2-NO_2 | CF_3 | H | =CH— | Cl | 196–198 |
| 52 | " | CH_3 | " | " | NO_2 | 218–221 |
| 53 | 2,4-(NO_2)_2 | " | " | " | Br | 193–200 |

TABLE 4-continued $$\underset{(X)_n}{\bigcirc}\text{—CONHCONH—}Q_2 \quad (Q_2: \underset{Y_1}{\overset{Y_2}{\bigcirc}}\text{—O—}\underset{N}{\overset{A}{\bigcirc}}\text{—Z})$$

| Compound No. | $(X)_n$ | $Y_1$ | $Y_2$ | A | Z | Melting point (°C.) |
|---|---|---|---|---|---|---|
| 54 | 2-NO$_2$-4-Cl | CF$_3$ | " | " | " | 213–216 |
| 55 | 2,4-(NO$_2$)$_2$ | " | " | " | CF$_3$ | 235–238 |
| 56 | 2-NO$_2$ | " | " | " | H | — |
| 57 | " | CF$_2$H | " | " | Cl | — |

The following compounds may be mentioned as compounds similar to those listed in Table 3.

Compound No. 58
N-(2-nitrobenzoyl)-N'-[2-methyl-3-(5-chloro-2-pyrimidinyloxy)phenyl]urea: Melting point 214°–216° C.

Compound No. 59
N-(2-nitrobenzoyl)-N'-[2-methyl-3-(5-bromo-2-pyrimidinyloxy)phenyl]urea: Melting point 202°–206° C.

The compounds of the present invention are effective against tumours such p-388 leukemia, L-1210 leukemia, B-16 melanoma, M-5076 sarcoma, colon 38, colon 26, Lewis lung carcinoma, etc. of test animals such as mice. On the other hand, certain in vivo testing systems and protocols have been developed by the National Cancer Institute for testing compounds to determine their suitability as antineoplastic agents. These have been reported in "Cancer Chemotherapy Reports", Part III, Vol. 3, No. 2 (1972), Deran, Greenberg, MacDonald, Schumacher and Abbott. These protocols have established standardized screening tests which are generally followed in the field of testing for antitumoral agents. Two of these systems are particularly significant to the present invention. They are lymphocyctic leukemia p388 and melanotic melanoma B16. These neoplasms are found in mice. Generally, good antitumor activity, shown in these protocols by a percentage increase of mean survival times of the treated (T) animals over the control (C) animals, is predictive of similar results in human leukemias. A mean survival time ratio T/C×100≧125% is considered necessary to demonstrate antineoplastic activity by the substance being tested.

Now, the antitumour activities, acute toxicity, doses and administration routes of the N-benzoylurea compounds of the present invention will be described.

(1) Antitumour activities

TEST EXAMPLE 1

(Intraperitoneal-intraperitoneal)

To BDF$_1$ mice, p-388 leukemia cells were intraperitoneally inoculated in an amount of 1×10$^6$ cells/mouse. A test drug was intraperitoneally administered twice, i.e. one day and four days after the inoculation. The mice were observed for 30 days for survival or death. The increase life span ILS (%)* of each treated group was obtained with the number of survival days of mice of the control group to which a physiological saline was administered, being evaluated as 0. The results are shown in Table 5. The drugs were dispersions obtained by adding small amounts of Z0 surfactants (e.g. Tween-80) to the test compounds.

TABLE 5

| Compound No. | Dose (Active ingredient mg/kg/day) | ILS * (%) |
|---|---|---|
| 1 | 25 | 88 |
|   | 12.5 | 67 |
| 2 | 100 | 99 |
| 3 | 50 | 126 |
|   | 12.5 | 74 |
| 5 | 12.5 | 75 |
| 8 | 50 | 39 |
| 9 | 200 | 42 |
| 17 | 6.25 | 91 |
| 20 | 25 | 68 |
|    | 12.5 | 33 |
| 23 | 12.5 | 45 |
| 25 | 400 | 56 |
| 26 | 12.5 | 95 |
| 27 | " | >153 |
| 28 | " | 84 |
| 29 | " | 132 |
| 30 | 50 | 74 |
| 32 | 100 | 105 |
| 33 | 200 | 107 |
| 35 | 100 | 84 |
| 36 | 12.5 | 89 |
| 37 | " | >143 |
| 45 | 200 | >118 |
| 51 | 25 | 60 |
|    | 12.5 | 41 |
| 52 | 50 | 80 |
| 53 | 50 | 106 |
| 55 | 50 | 74 |

Note:
ILS (%)*: Increase Life Span, calculated in accordance with the following formula: ILS (%) ILS(%) = MST-100, where MST is the ratio of median survival time of test and control animals.

TEST EXAMPLE 2

(intraperitoneal-oral)

To BDF$_1$ mice, p-388 leukemia cells were intraperitoneally inoculated in an amount of 1×10$^6$ cells/mouse. A test drug was orally administered twice i.e. one day and four days after the inoculation. The mice were observed for 30 days for survival or death, and the ILS (%) of each treated group was obtained with the number of survival days of mice of the control group to which a physiological saline was administered, being evaluated as 0. The results are shown in Tables 6-1, , 6-2 and 6-3. The test drugs and comparative drugs were formulated in accordance with Formulation Example 4 given hereinafter.

TABLE 6-1

| Compound No. | Dose (Active ingredient mg/kg/day) | ILS (%)* |
| --- | --- | --- |
| 1 | 100 | 90 |
|   | 50 | 67 |
| 3 | 400 | 114 |
|   | 200 | 76 |
| 4 | 100 | 111 |
| 5 | 100 | 101 |
|   | 50 | 55 |
| 17 | 12.5 | 111 |
| 20 | 200 | 84 |

TABLE 6-2

| Compound No. | Dose (Active ingredient mg/kg/day) | ILS (%)* |
| --- | --- | --- |
| 23 | 12.5 | 147 |
| 24 | 25 | 104 |
|   | 12.5 | 48 |
| 26 | 200 | 32 |
| 27 | 100 | 126 |
|   | 50 | 51 |
| 28 | 50 | 126 |
| 29 | 50 | 116 |
|   | 25 | 72 |
| 30 | 800 | 114 |
| 34 | 25 | 78 |
| 36 | 200 | 55 |
| 37 | 25 | 159 |
| 38 | 200 | 118 |
| Comparative Compound No. 1 | 1600 | 86 |
|   | 800 | 43 |
|   | 400 | 16 |
| Comparative Compound No. 2 | 1600 | 24 |
|   | 800 | 11 |
|   | 400 | 13 |

TABLE 6-3

| Compound No. | Dose (Active ingredient mg/kg/day) | ILS (%)* |
| --- | --- | --- |
| 51 | 800 | 67 |
|   | 400 | 38 |
| 52 | 800 | 39 |
|   | 400 | 37 |
| 53 | 400 | 184 |
|   | 200 | 103 |
| Comparative Compound No. 3 | 1600 | 11 |
|   | 800 | 2 |

Notes:
ILS (%)* is the same as mentioned above in Table 5.

Comparative Compound No. 1:
N-(2-nitrobenzoyl)-N,-[3-chloro-4-(5-iodo-2-pyrimidinyloxy)phenyl]urea, disclosed in Japanese Unexamined Patent Publication No. 109721/1982.

Comparative Compound No. 2
N-(2-chlorobenzoyl)-N'-[3-chloro-4-(5-chloro-2-pyrimidinyloxy)phenyl]urea, disclosed in Japanese Unexamined Patent Publication No. 109721/1982.

Comparative Compound No. 3
N-(2-nitrobenzoyl)-N'-[3-chloro-4-(5-trifluoromethyl-2-pyridyloxy)phenyl]urea, disclosed in Japanese Unexamined Patent Publication Nos. 31664/1982 and 109721/1982.

TEST EXAMPLE 3

(intraperitoneal-oral)

To BDF$_1$ mice, L-1210 leukemia cells were intraperitoneally inoculated in an amount of $1 \times 10^5$ cells/mouse. A test drug was orally administered twice i.e. one day and eight days after the inoculation. The mice were observed for 30 days for survival or death, and the ILS (%) of each treated group was obtained with the number of survival days of mice of the control group to which a physiological saline was administered, being evaluated as 0. The results are shown in Table 7. The test drugs and comparative drugs were formulated in accordance with Formulation Example 4 given hereinafter.

TABLE 7

| Compound No. | Dose (Active ingredient mg/kg/day) | ILS (%)* |
| --- | --- | --- |
| 1 | 100 | 112 |
| 5 | 200 | 60 |
| 23 | 25 | 76 |
|   | 12.5 | 56 |
| 24 | 50 | 137 |
|   | 25 | 77 |
| 27 | 50 | 47 |
| 30 | 400 | 137 |
|   | 200 | 51 |
| 37 | 25 | 90 |
|   | 12.5 | 51 |
| Comparative Compound No. 1 | 800 | 30 |

Note:
ILS (%) is the same as mentioned in Table 5 and Comparative Compound No. 1 is the same as mentioned in Table 6-2.

TEST EXAMPLE 4

(intraperitoneal-oral)

To BDF$_1$ mice, a suspension of B-16 melanoma cells were intraperitoneally inoculated in an amount of 0.5 ml/mouse. A test drug was orally administered three times i.e. one day, eight days and fifteen days after the inoculation. The mice were observed for 60 days for survival or death, and the ILS (%) of each treated group was obtained with the number of survival days of mice of the control group to which a physiological saline was administered, being evaluated as 0. The results are shown in Table 8. The test drugs were formulated in accordance with Formulation Example 4 given hereinafter. The suspension of B-16 melanoma cells was prepared by taking out under an aseptic condition the tumour cells successively subcutaneously transplanted in C57BL/6 mice, passing the tumour cells through a stainless steel mesh and suspending 1 g of the tumour cells in 9 ml of an isotonic solution such as a culture medium or a physiological saline.

TABLE 8

| Compound No. | Dose (Active ingredient mg/kg/day) | ILS (%)* |
| --- | --- | --- |
| 1 | 100 | 49 |
|   | 50 | 36 |
| 23 | 25 | 76 |
|   | 12.5 | 44 |
| 37 | 25 | 56 |
|   | 12.5 | 37 |

Note:
ILS (%) is the same as mentioned in Table 5.

TEST EXAMPLE 5

(intraperitoneal-oral)

To BCF$_I$ mice, M-5076 sarcoma cells were intraperitoneally inoculated in an amount of $1 \times 10^6$ cells/mouse. A test drug was orally administered three times i.e. one day, eight days and fifteen days after the inoculation. The mice were observed for 60 days for survival or death, and the ILS (%) of each treated group was obtained with the number of survival days of mice of the control group to which a physiological saline was administered, being evaluated as 0. The results are shown in Table 9. The test drugs and comparative drugs were formulated in accordance with Formulation Example 4 given hereinafter.

TABLE 9

| Compound No. | Dose (Active ingredient mg/kg/day) | ILS (%)* |
| --- | --- | --- |
| 1 | 50 | 38 |
| 23 | 25 | 107 |
|  | 12.5 | 82 |

Note:
ILS (%) is the same as mentioned in Table 5.

The compounds of the present invention exhibit high antitumour activities whether the diseased portions and the portions to which the drugs are administered, are the same or different. The reason is not clearly understood, but it is assumed that the excellent antitumour activities are attributable to that the compounds of the invention are superior in the absorption of the drugs by the gut, in the drug concentrations in blood and in the transfer property of the drugs to the target portions.

(2) Acute toxicity:

To ddY mice, a drug containing one of Compound Nos. 1, 5, 20, 23, 26–29, 36 and 37 of the present invention formulated in accordance with Formulation Example 4 was intraperitoneally administered, and the LD50 value was measured and found to be at least 25 mg/kg in each case. The $LD_{50}$ value of Compound No. 51 of the invention was found to be at least 50 mg/kg, that of each of Compound Nos. 3, 8, 30, 31, 39, 52, 53 and 54 was found to be at least 100 mg/kg, and that of each of Compound Nos. 2, 9, 25, 32, 33, 35, 45 and 55 was found to be at least 400 mg/kg.

(3) Doses and administration routes

As to administration routes in the case of animals, the compounds of this invention are administered as injections such as intraperitoneal injection, intravenous injection, local injection and the like, or as oral drugs. In the case of human beings, said compounds are administered as injections such as intravascular (intravenous or intraarterial) injection, local injection and the like, or oral drugs, suppositories or the like. As to the dose, said compounds are administered continuously or intermittently in a range in which the total dose does not exceed a certain level, in consideration of the results of animal experiments and various conditions. However, the dose may, of course, be properly varied depending on the administration route and on the conditions of a patient or an animal to be treated (for example, age, body weight, sex, sensitivity, food and the like), interval of administration drugs used in combination with said compounds and the degree of disease. An optimum dose and the number of administrations under certain conditions should be determined by medical specialists.

The antitumorous composition of this invention are prepared in the same manner as for conventional drugs. For example, they are prepared from an active ingredient and various pharmacologically acceptable adjuvants such as inactive diluent and the like. Oral and intravenous administration of these antitumorous compositions is most suitable. The content of the active ingredient in the antitumorous compositions of this invention may vary depending on various conditions and cannot be determined uniquely. It is sufficient that the active ingredient is contained similarly to the case of conventional antitumorous compositions. For instance, the composition may contain at least 0.001% by weight.

The compounds of the present invention are hardly soluble in both water and organic solvents. Therefore, they are preferably formulated into an aqueous suspension which may further contain phospholipids. As a method for producing an aqueous suspension containing no phospholipids, there may be mentioned a method wherein, if necessary, the active compound is preliminarily pulverized into fine powder, then the fine powder of the active compound is added to an aqueous solution containing a surfactant and, if necessary, a defoaming agent, the mixture is pulverized in a wet system until all particles have a particle size of not higher than 5 μm, more preferably not higher than 2 μm (80% of particles), and a thickener is added thereto. As specific examples of the surfactant, there may be mentioned an oxyethylated polyarylphenol phosphate, a polyoxyethylene hardened castor oil, a polyoxyethylene sorbitan fatty acid ester, a sugar ester, a polyoxyethylene polyoxypropylene block polymer, etc. As specific examples of the defoaming agent, there may be mentioned dimethylpolysiloxane, methylphenylsiloxane, a sorbitan fatty acid ester, a polyoxyethylenepolyoxypropylene cetyl ether, silicone, etc. As specific examples of the thickener, there may be mentioned guar gum, alginic acid, gum arabic, pectin, starch, xanthane gum, gelatin, etc. On the other hand, as a method for preparing an aqueous suspension containing a phospholipid, there may be mentioned a method wherein a phospholipid such as soybean phospholipid or yolk phospholipid is used instead of the surfactant in the above-mentioned method, and an antioxidant such as o-tocopherol is used instead of the thickener.

Further, these compounds may be formulated into tablets, capsules, enteric agents, granules, powders, injection solutions or suppositories by common methods for formulations.

Now, Formulation Examples of the antitumour drugs of the present invention will be described.

FORMULATION EXAMPLE 1

70 mg of a non-crystalline powder of the above Compound No. 9 or 23 was thoroughly mixed with 30 mg of lactose, and 100 mg of the mixture was filled into a capsule to obtain a capsule drug for oral administration.

FORMULATION EXAMPLE 2

85 parts by weight of a non-crystalline powder of the above Compound No. 3 or 24 was uniformly mixed with 1 part by weight of glucose, 10 parts by weight of corn starch and 1.5 parts by weight of a 5% starch paste, and the mixture was granulated by a wet method. Then, 1 part by weight of magnesium stearate was added thereto. The mixture was tableted to obtain tablets for oral administration.

FORMULATION EXAMPLE 3

5 g of the above Compound No. 2 or 29 was dissolved in 5 ml of dimethylacetamide, and 25 ml of coconut oil, 7 g of Pegnol HC-17 (manufactured by Toho Kagaku K.K.) and 6 g of HO-10M (manufactured by Toho Kagaku K.K.) were added to obtain an emulsion. To this emulsion, the same amount of sterilized distilled water was added, and the mixture was subjected to ultrasonic treatment for from 20 to 30 seconds to obtain an oily suspension.

FORMULATION EXAMPLE 4

The Compound No. 1 or 23 of the present invention was preliminarily pulverized by a centrifugal pulverizer. On the other hand, 5 parts by weight of polyoxyethylene (60) hardened castor oil, 0.2 part by weight of silicone and 0.3 part by weight of a polyoxyethylene-polyoxypropylene block polymer were added to 79.5 parts by weight of a physiological saline to obtain an aqueous solution, to which 10 parts by weight of the above pulverized Compound No. 1 or 23 of the present invention was added. The mixture was pulverized in a wet system by a sand mill using glass beads (80% of particles having a particle size of not larger than 2 μm). Then, 5 parts by weight of xanthane gum (2% solution) was added thereto to obtain an aqueous suspension.

FORMULATION EXAMPLE 5

To an aqueous solution obtained by dissolving 1.5 parts by weight of oxyethylated polyarylphenol phosphate and 0.2 part by weight of silicone in 53.3 parts by weight of a physiological saline, 40 parts by weight of the Compound No. 5 or 25 of the present invention was added, and the mixture was pulverized in a wet system in the sand mill by using glass beads (90% of particles having a particle size of not larger than 2 μm). Then, 5 parts by weight of xanthane gum (2% solution) was added thereto to obtain an aqueous suspension.

FORMULATION EXAMPLE b 6

The Compound No. 1 of the present invention was preliminarily pulverized by a centrifugal pulverizer. 5 parts by weight of the pulverized Compound No. 1 of the present invention was added to an aqueous solution obtained by stirring and dispersing 2 parts by weight of yolk phospholipid, 0.001 part by weight of α-tocopherol and 92.999 parts by weight of a physiological saline. Then, the mixture was pulverized in a wet system in a sand mill by using glass beads (80% of particles having particle size of not larger than 2 μm) to obtain an aqueous suspension.

FORMULATION EXAMPLE 7

The Compound No. 37 of the present invention was preliminarily pulverized by a centrifugal pulverizer. On the other hand, 5 parts by weight of polyoxyethylene (60) hardened castor oil were added to 60 parts by weight of a physiological saline to obtain an aqueous solution, to which 30 parts by weight of the above pulverized Compound No. 37 of the present invention was added. The mixture was pulverized in a wet system by a sand mill using glass beads (80% of particles having a particle size of not larger than 2 μm). Then, 5 parts by weight of xanthane gum (2% solution) was added thereto to obtain an aqueous suspension.

FORMULATION EXAMPLE 8

To an aqueous solution obtained by dissolving 1.5 parts by weight of oxytethylated polyarylphenol phosphate, 0.2 part by weight of silicone and 0.3 part by weight of a polyethylene-polyoxypropylene block polymer in 81 parts by weight of a physiological saline, 10 parts by weight of the Compound No. 23 of the present invention was added, and the mixture was pulverized in a wet system in the sand mill by using glass beads (90% of particles having a particle size of not larger than 2 μm). Then, 7 parts by weight of xanthane gum (2% solution) was added thereto to obtain an aqueous suspension.

We claim:
1. An N-benzoyl urea compound having the formula:

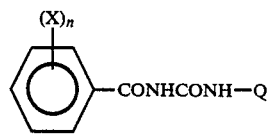

wherein X is a hydrogen atom, a halogen atom or a nitro group, n is an integer of from 1 to 3, and Q is

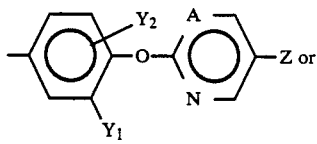

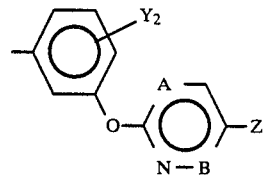

wherein $Y_1$ is alkyl, alkoxy or alkoxycarbonyl or said alkyl, said alkoxy or said alkoxycarbonyl substituted by at least one group selected from the group consisting of halogen, alkoxy, alkylthio, cyano and thiocyanate; $Y_2$ is hydrogen, halogen, nitro, alkyl, alkoxy or alkoxycarbonyl, or said alkyl, said alkoxy or said alkoxycarbonyl substituted by at least one group selected from the group consisting of halogen, alkoxy, alkylthio, cyano and thiocyanate; Z is hydrogen, halogen, trifluoromethyl or nitro, and each of A and B is =CH— or nitrogen, provided that one of A and B is =C— and the other is nitrogen, with the provisos (1) that when Q is

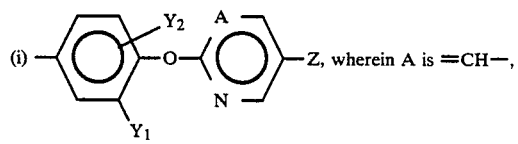

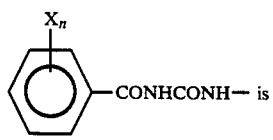

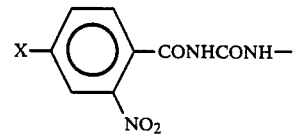

where (ii) when X is hydrogen and $Y_1$ is alkyl, Z is not hydrogen, halogen or trifluoromethyl; and (2) that when Q is

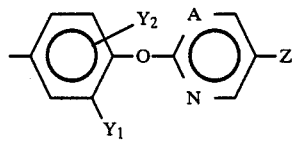

wherein A is nitrogen and $Y_l$ is trifluoromethyl, $Y_2$ is other than hydrogen and wherein the alkyl groups and the alkyl portions of said alkoxy and alkoxycarbonyl groups have from 1 to 6 carbon atoms.

2. The N-benzoyl urea compound according to claim 1, wherein said $C_{1-6}$ group is methyl, ethyl, propyl, butyl, pentyl or hexyl.

3. The N-benzoyl urea compound according to claim 1, wherein Q is

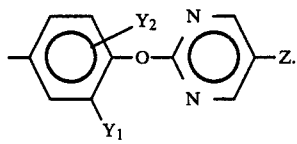

4. The N-benzoyl urea compound according to claim 2, wherein X is nitro or halogen, $Y_1$ is alkyl or alkyl substituted by halogen, $Y_2$ is hydrogen, and Z is halogen.

5. The N-benzoyl urea compound according to claim 1, wherein Q is

6. The N-benzoyl urea compound according to claim 5, wherein $Y_2$ is alkyl or alkyl substituted by halogen, A is nitrogen, B is =CH—, and Z is halogen.

7. The compound according to claim 3, which is N-(2-nitrobenzoyl)-N,-[4-(5-chloro-2-pyrimidinyloxy)-3-methylphenyl]urea.

8. The compound according to claim 3, which is N-(2-nitrobenzoyl)-N'-[4-(5-bromo-2-pyrimidinyloxy)-3-methylphenyl]urea.

9. The compound according to claim 5, which is N-(2-nitrobenzoyl)-N'-[4-(5-chloro-2-pyrimidinyloxy)-4-methylphenyl]urea.

10. An antitumorous composition which is effective against p-388 leukemia, L-1210 leukemia, B-16 melanoma, or M-5076 sarcoma in a mouse, comprising:
a therapeutically effective amount of an N-benzoyl urea compound as defined in claim 1 and a pharmaceutically acceptable adjuvant.

11. A method for treating p-388 leukemia, L- 1210 leukemia, B-16 melanoma, or M-5076 sarcoma in a mouse, which comprises:
administering a therapeutically effective amount of an N-benzoyl urea compound as defined in claim 1 to a diseased subject.

* * * * *